US008390244B2

(12) United States Patent
Wooley et al.

(10) Patent No.: US 8,390,244 B2
(45) Date of Patent: Mar. 5, 2013

(54) RECHARGEABLE BATTERY BACKUP APPARATUS AND METHOD FOR INSULIN PUMP

(75) Inventors: Richard Wooley, Coral Springs, FL (US); Roy Morgan, Weston, FL (US); Colin Jackson, Sunrise, FL (US)

(73) Assignee: Nipro Healthcare Systems, LLC, Fort Lauderdale, FL (US)

( * ) Notice: Subject to any disclaimer, the term of this patent is extended or adjusted under 35 U.S.C. 154(b) by 1009 days.

(21) Appl. No.: 11/731,483

(22) Filed: Mar. 30, 2007

(65) Prior Publication Data

US 2008/0243079 A1 Oct. 2, 2008

(51) Int. Cl.
*H02J 7/00* (2006.01)
(52) U.S. Cl. .......................... 320/103; 320/101; 307/66
(58) Field of Classification Search .................. 320/103; 604/154
See application file for complete search history.

(56) References Cited

U.S. PATENT DOCUMENTS

| | | | |
|---|---|---|---|
| 4,685,903 A | 8/1987 | Cable et al. | |
| 4,692,145 A * | 9/1987 | Weyant | 604/65 |
| 5,244,463 A | 9/1993 | Cordner, Jr. et al. | |
| 5,321,392 A * | 6/1994 | Skakoon et al. | 340/636.1 |
| 5,497,772 A | 3/1996 | Schulman et al. | |
| 5,574,436 A * | 11/1996 | Sisselman et al. | 340/663 |
| 5,582,593 A | 12/1996 | Hultman | |
| 5,628,619 A | 5/1997 | Wilson | |
| 5,658,250 A | 8/1997 | Blomquist et al. | |
| 5,683,367 A | 11/1997 | Jordan et al. | |
| 5,712,795 A | 1/1998 | Layman et al. | |
| 5,764,034 A | 6/1998 | Bowman et al. | |
| 5,791,880 A | 8/1998 | Wilson | |
| 5,867,006 A * | 2/1999 | Dias et al. | 320/106 |
| 6,183,412 B1 | 2/2001 | Benkowski et al. | |
| 6,423,035 B1 * | 7/2002 | Das et al. | 604/155 |
| 6,462,507 B2 * | 10/2002 | Fisher, Jr. | 320/101 |
| 6,648,821 B2 | 11/2003 | Lebel et al. | |
| 6,902,837 B2 | 6/2005 | McCluskey et al. | |
| 6,977,479 B2 * | 12/2005 | Hsu | 320/101 |
| 7,001,359 B2 | 2/2006 | Rogers | |
| 7,048,715 B2 | 5/2006 | Diaz et al. | |
| 7,070,577 B1 | 7/2006 | Haller et al. | |
| 7,122,026 B2 | 10/2006 | Rogers et al. | |
| 7,638,975 B2 * | 12/2009 | Nakamiya et al. | 320/134 |
| 7,737,581 B2 * | 6/2010 | Spurlin et al. | 307/66 |
| 2006/0091860 A1 * | 5/2006 | Nakamiya et al. | 320/128 |
| 2007/0040449 A1 * | 2/2007 | Spurlin et al. | 307/64 |

* cited by examiner

*Primary Examiner* — Ramy Ramadan
(74) *Attorney, Agent, or Firm* — Finnegan, Henderson, Farabow, Garrett & Dunner LLP

(57) ABSTRACT

An apparatus and method for allowing an operator of a portable infusion device continue to operate the device after the primary battery source becomes depleted. The invention contemplates providing a secondary, rechargeable battery in addition to the primary battery, to allow the infusion device to operate even in the instance of a sudden drop in primary battery voltage. The apparatus includes a housing accommodating a syringe, where the syringe contains a liquid to be infused. Also included is a motor, a drive system operatively connected to the motor, where the drive system advances a piston of the syringe in order to expel the liquid from a barrel of the syringe. A power source is in electrical contact with and supplies power to the motor. The power source includes a primary battery module, and a rechargeable battery module, wherein the primary battery source supplies power to the rechargeable battery module. The result is a fail-safe system of alerting the user of low or critical battery conditions.

5 Claims, 3 Drawing Sheets

RECHARGEABLE BATTERY BACKUP APPARATUS AND METHOD FOR INSULIN PUMP

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to an apparatus and method for detecting a low or critical battery condition in an infusion pump by providing a backup, rechargeable battery and for allowing the user to continue use of the infusion pump even after the depletion of the primary battery.

BACKGROUND OF THE INVENTION

Insulin pump systems allow patients to administer safe doses of an intravenous or subcutaneous medication at will, without the need for constant supervision by medical staff. These devices often include a housing that houses a cartridge, a motor, a drive system, and a power supply, such as a battery, which supplies power to the motor. The outside of the housing provides key pad entry for allowing the patient to program the rate of insulin delivery and to modify the delivery rate according to the patient's expected or actual carbohydrate intake.

Recent changes in disposable battery design have resulted in battery voltage curves that remain substantially constant throughout the life of the battery. While the voltage of older types of disposable battery chemistry enables voltages to decrease gradually with use, new disposable batteries remain consistent throughout the battery's life until a short drop-off in voltage occurs. While this may prove to be harmless for certain products, it can be devastating to a portable insulin pump user. Portable insulin pump users rely on the infusion of insulin at preprogrammed times. A low battery condition may lead to an incorrect dosage or even lead to a missed dosage, resulting in an insulin pump that stops operating without warning. The results can obviously be devastating to the user.

International Standards IEC 60601-2-24 and 60601-1-8 govern the general requirements, tests and guidance for alarm system in medical electrical equipment, including infusion pumps and controllers. These standards require that infusion pumps include adequate alarm systems to notify the user when a low or critical battery condition is about to occur. However, it has recently become increasingly difficult to detect critical battery conditions with new disposable batteries in a timely matter due to the severe and sudden decline in voltage at the end of battery life. Because of the rapid decrease in voltage of disposable batteries onboard the insulin pump, there is currently no adequate means to detect a low or critical battery voltage condition.

Therefore, what is needed is an apparatus and method that can detect a low or critical battery condition in an infusion pump in a timely manner and can allow the user to continue to operate for a period of time after the primary disposable battery becomes depleted.

SUMMARY OF THE INVENTION

The present invention advantageously provides an apparatus and method for allowing an operator of a portable infusion device continue to operate the device after the primary battery source becomes depleted. The invention contemplates providing a secondary, rechargeable battery in addition to the primary battery, to allow the infusion device to operate even in the instance of a sudden drop in primary battery voltage. The result is a fail-safe system of alerting the user of low or critical battery conditions.

In one embodiment, an infusion pump is provided where the infusion pump includes a housing accommodating a syringe, where the syringe contains a liquid to be infused, a motor within the housing, a drive system operatively connected to the motor, where the drive system advances a piston of the syringe to expel the liquid from a barrel of the syringe, and a power source, in electrical contact with and supplying power to the motor. The power source includes a primary battery module, and a rechargeable battery module, wherein the primary battery source supplies power to the rechargeable battery module.

In another embodiment, a power source module for use in an infusion pump is provided. The power source includes a primary battery, a rechargeable battery, a recharging circuit for recharging the rechargeable battery, a power source selector module for selecting one of the primary battery or the rechargeable battery, and one or more voltage converters.

In yet another embodiment, a method of detecting a critical primary battery condition in an infusion pump is provided. The method includes providing a rechargeable battery, providing a primary battery, wherein the infusion pump is initially powered via the primary battery, detecting when the primary battery reaches a critical battery condition, upon the primary battery reaching the critical battery condition, powering the infusion pump via the rechargeable battery.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein.

DETAILED DESCRIPTION OF THE PREFERRED EMBODIMENTS

Figure 1:
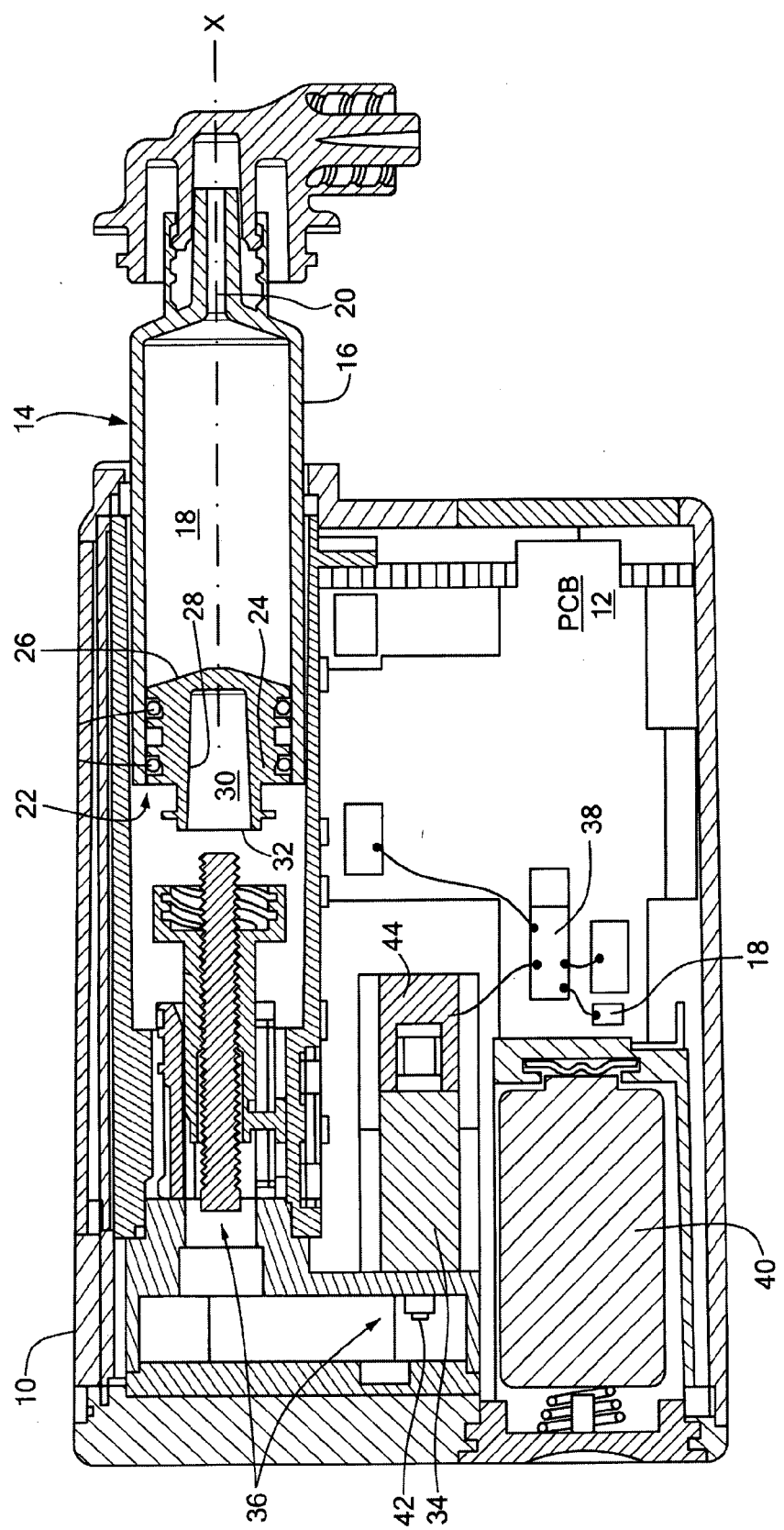
FIG. 1 is a side sectional view of an infusion pump system according to the present invention.

With reference to FIG. 1, a portable pump apparatus for use in an ambulatory injection system, such as an insulin injection system, is shown. The apparatus includes a housing 10, which is designed to fit conveniently in the pocket of a user or to be attached to a belt clip. A cassette 14, such as a disposable or reusable syringe, is selectively received within the housing 10. The syringe 14 holds a supply of a medicament, such as insulin, for injection into a diabetic person, or other user in need of the medicament. The syringe 14 includes a barrel 16, which defines an internal chamber 18 for holding the medicament, a dispensing outlet 20 connected with one end of the barrel 16, and an opening 22 at an opposite end of the barrel 16. A plunger or piston 24 is received within the barrel 16 via the opening 22 for reciprocal motion within the barrel 16 for ejecting the medicament from the barrel. The piston 24 includes a head portion or cap 26, which seals the opening 22, and a longitudinally extending cylindrical or frustoconical portion 28, extending from the head portion, which defines an internal piston chamber 30 with an open end 32 furthest from the barrel 16.

Mounted within the housing 10, are a motor 34 and a drive system 36 for incrementally advancing the piston 24 to eject aliquots of the medicament according to a preprogrammed injection schedule. The motor 34 is under the control of a microprocessor-controller 38, which is preferably housed within the housing 10. Power for the motor and other operative components of the pump system is supplied by a battery 40, or other source of power. The motor 34 is preferably a stepper motor, which rotates in finite, small increments or steps. The drive system 36 includes a drive shaft 42, which is coupled to the motor so that it rotates a small portion of a revolution with each step of the motor. For example, the motor 34 may advance twenty steps to turn the drive shaft 42 one complete revolution. As shown in FIG. 1, the drive shaft 42 is aligned generally concentrically with the longitudinal axis x of the syringe barrel 16 and piston 24 and rotates generally about this axis.

An encoder 50 is attached to an armature of the motor 34 to detect when the steps (i.e., rotations) are occurring. For example, a two-phase encoder alternatively registers a "zero" or a "one" output with each successive step of the encoder. The microprocessor-controller 38 is equipped with processing software or hardware to detect the change in output of the encoder and thereby determine whether the motor 34 is advancing as instructed.

Figure 2:
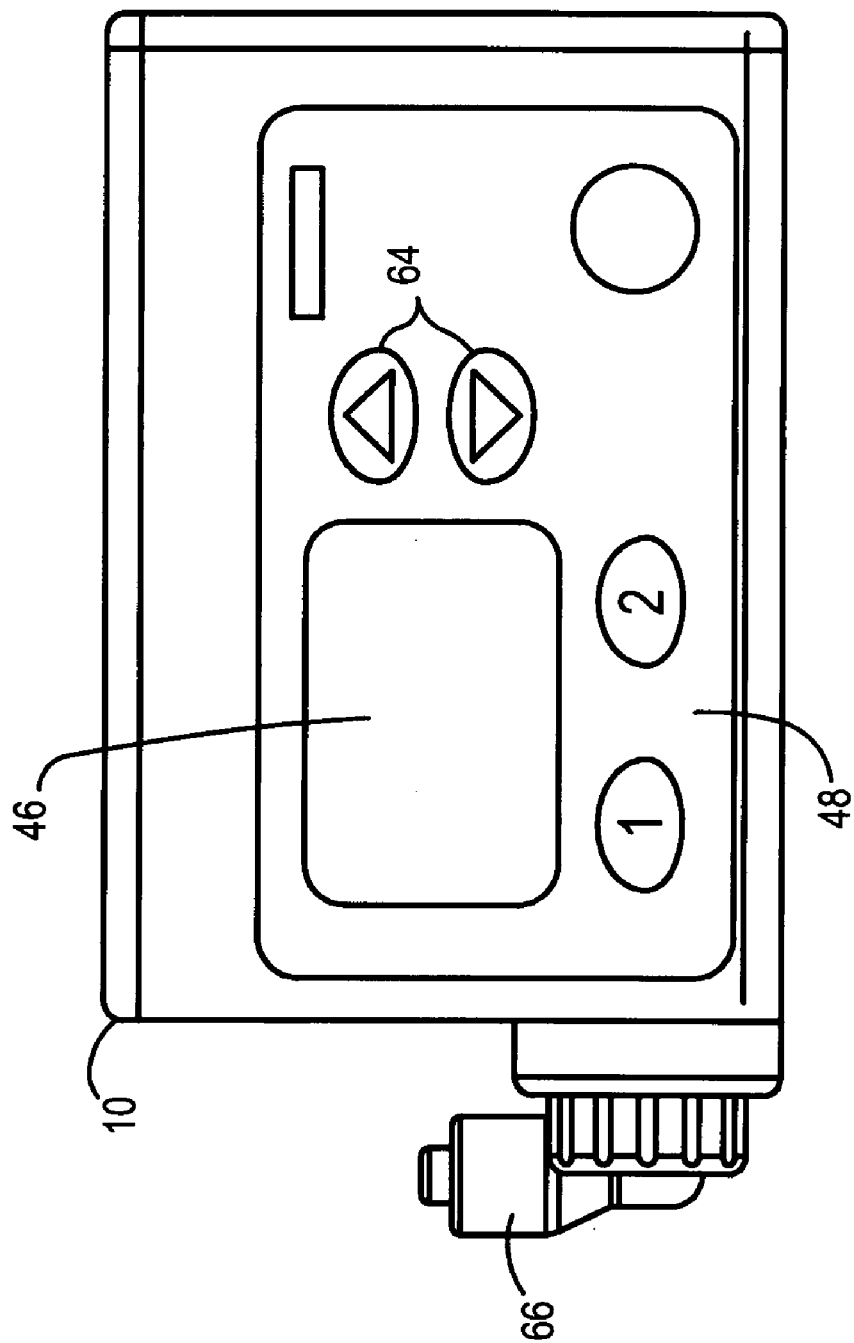
FIG. 2 is a top view of the infusion pump of FIG. 1.

FIG. 2 shows a top view of an insulin pump that incorporates the present invention. Housing 10 can be comprised of plastic or any other type of shatter-resistant material. Housing 10 may also be waterproof. Screen 46 allows the user to view such indicators such as the current basal rate, the amount and time of the previous bolus, the insulin volume and the current date and time settings. The up and down buttons 64 may be used in order illuminate the pump's screen 46. This allows for easy viewing of the pump's menus and messages. Infusion set 66 connects to the syringe cap at an approximate 90 degree angle to protect the luer-lock connector and to protect the user against inadvertent injury.

Figure 3:
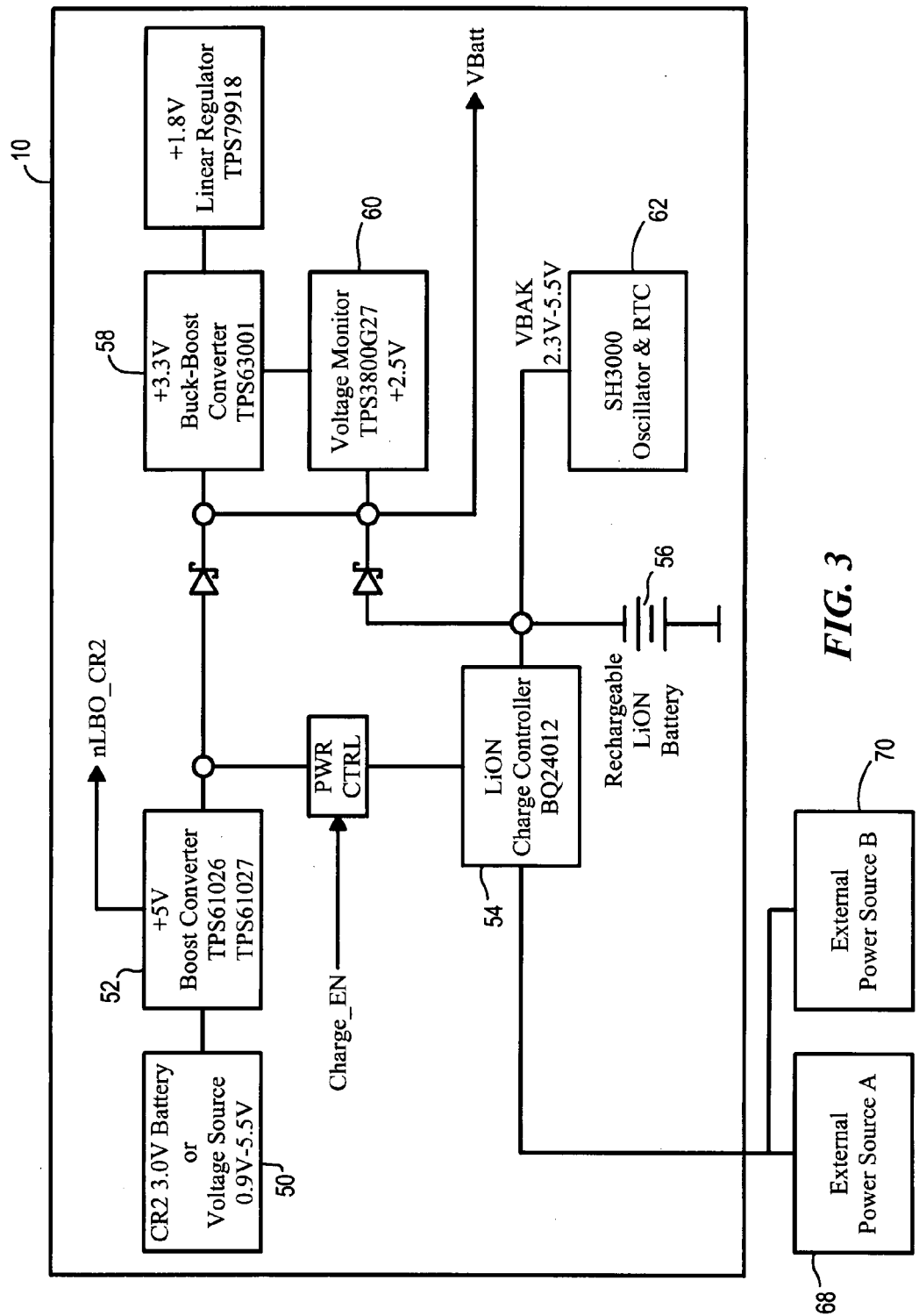
FIG. 3 is an electrical schematic illustrating the power source of the present invention.

FIG. 3 is an electrical schematic illustrating the power source of the present invention. A primary power source 50, such as a CR2 battery, supplies power to the infusion pump 10. The primary battery powers a +5V boost converter 52. The output of the boost converter 52 is regulated to +5 volts and supplies power to both a Li-Ion charge controller 54 and a DC-DC converter 58, such as a +3.3 DC-DC buck-boost converter.

The Li-Ion charge controller 54 controls the charging of a rechargeable battery 56. The rechargeable battery 56 could be, for example, a Lithium Ion (Li-Ion) rechargeable battery. The rechargeable battery 56 supplies power to the buck-boost converter 58 through one or more diodes 64. This occurs at times when the CR2 battery 50 reaches a critical voltage level, is removed or is exhausted. A critical battery level can be any predefined voltage level. Rechargeable battery 56 may also supply backup power to a clock 62, such as SH3000 Real Time Clock (RTC). A voltage monitor 60 turns off the buck-boost converter 58 in order to save the final energy remaining in the rechargeable battery 56 for use by the RTC 62.

Charge controller 54 can also provide multiple switching to more than one input source of power for charging the Li-Ion rechargeable battery 56. More specifically, such external charging power sources 68, 70 can employ connection to external power conversion components that include, for example, photo-electric generation cells, photo-voltaics, fuel cells, peltier thermo-electric converters and the like. As such, external environmentally available energy sources can be used to maintain trickle charge to the Li-Ion battery 56 and maintain it's longevity of charge for greater periods of time. This functionality obviates the need for manual attendance to periodic replacement of the disposable batteries to maintain rechargeable Li-Ion battery charge above the minimum charge level (i.e., 0.8V) below which can lead to permanent battery curve degradation. Such functionality allows the user of the insulin infusion pump to subject the unit to extended periods of storage so long as the storage conditions provide the necessary environmental energy input (i.e. light, heat, etc.).

It should be noted that the schematic illustration of FIG. 3 is an exemplary embodiment of the power supply of the present invention. Variations of the schematic of FIG. 3 are within the scope of the invention. The system described herein provides a rechargeable battery 56 that serves as a backup energy source to primary battery 50. Because of the rapid voltage decrease in modern disposable batteries, electrical medical devices such as infusion pumps cannot adequately warn the user of a low or critical battery level in enough time to allow the user to take corrective action, i.e., replace the primary battery. The use of a second, rechargeable battery 56 will allow the infusion pump to continue normal operation and enable the initiation of an alarm indicating when a low or critical battery level has been reached, thus giving the user enough time to take corrective action without the danger of the infusion pump completely shutting down.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An infusion pump comprising:
a housing accommodating a syringe, the syringe containing a liquid to be infused;
a motor within the housing;
a drive system operatively connected to the motor, the drive system to advance a piston of the syringe to expel the liquid from a barrel of the syringe; and
a power source in electrical contact with and supplying power to the motor, the power source comprising:
a primary battery module;
a rechargeable battery module, wherein the primary battery source supplies power to the rechargeable battery module;
a first DC-DC converter module in electrical communication with the primary battery module; and
a charge controller in electrical communication with the first DC-DC converter module and the rechargeable battery module; wherein the charge controller is in electrical communication with one or more external power sources for charging the rechargeable battery module, wherein the first DC-DC converter supplies power to the charge controller and a second DC-DC converter and wherein the charge controller is configured to maintain a trickle charge from the one or more external power sources to the rechargeable battery module.

2. The infusion pump of claim 1, wherein the power source further comprises at least one diode, wherein if the primary battery module reaches a critical condition, the rechargeable battery module supplies power to the second DC-DC converter via the at least one diode.

3. The infusion pump of claim 2, wherein the power source further comprises a voltage monitor unit, the voltage monitor configured to switch off the second DC-DC converter to preserve energy remaining in the rechargeable battery.

4. The infusion pump of claim 1, wherein at least one of the one or more external power sources is a photovoltaic power source.

5. The infusion pump of claim 1, wherein at least one of the one or more external power sources is a thermoelectric power source.

* * * * *